United States Patent
Son et al.

(10) Patent No.: US 11,844,507 B2
(45) Date of Patent: Dec. 19, 2023

(54) FLAT-TYPE SLEEVE ANCHOR

(71) Applicant: ARC KOREA CO., LTD.

(72) Inventors: Min-Ah Son, Gyeonggi-do (KR); Jung-Ah Son, Gyeonggi-do (KR)

(73) Assignee: ARC KOREA CO., LTD., Gyeonggi-do (KR)

( * ) Notice: Subject to any disclaimer, the term of this patent is extended or adjusted under 35 U.S.C. 154(b) by 828 days.

(21) Appl. No.: 15/734,453

(22) PCT Filed: Aug. 29, 2018

(86) PCT No.: PCT/KR2018/009968
§ 371 (c)(1),
(2) Date: Dec. 2, 2020

(87) PCT Pub. No.: WO2019/139215
PCT Pub. Date: Jul. 18, 2019

(65) Prior Publication Data
US 2021/0219971 A1    Jul. 22, 2021

(30) Foreign Application Priority Data

Jan. 12, 2018   (KR) .................. 10-2018-0004675

(51) Int. Cl.
*A61B 17/04*    (2006.01)

(52) U.S. Cl.
CPC .. *A61B 17/0401* (2013.01); *A61B 2017/0414* (2013.01); *A61B 2017/0458* (2013.01); *A61B 2017/0464* (2013.01)

(58) Field of Classification Search
CPC ..... A61B 17/04; A61B 17/0401; A61B 17/70; A61B 2017/0409; A61B 2017/0458; A61B 2017/0414; A61B 2017/0464
See application file for complete search history.

(56) References Cited

U.S. PATENT DOCUMENTS

| 4,510,934 A * | 4/1985 | Batra ............... A61B 17/06166 |
| | | 428/377 |
| 9,421,008 B2 * | 8/2016 | Burkhart ........... A61B 17/0401 |
| 2014/0277130 A1 | 9/2014 | Housman | |

FOREIGN PATENT DOCUMENTS

| KR | 1020150136707 | 12/2015 |
| KR | 101634796 | 6/2016 |

\* cited by examiner

*Primary Examiner* — Vi X Nguyen
(74) *Attorney, Agent, or Firm* — IPLA P.A.

(57) ABSTRACT

A flat-type sleeve anchor is shape-deformed after being inserted into a bone so as to fix, to the bone, soft tissues such as tendons, ligaments, and muscles and, particularly, to a flat-type sleeve anchor which employs an anchor body made of a flat material, so that the anchor can be easily inserted into a bond and then shape-deformed.

5 Claims, 4 Drawing Sheets

(a)

(b)

(c)

(d)

(a)  (b)

FLAT-TYPE SLEEVE ANCHOR

BACKGROUND

The present invention relates to a flat-type sleeve anchor which is transformed after being inserted into a bone so as to fix soft tissues such as tendons, ligaments and muscles to the bone. In particular, the present invention relates to a flat-type sleeve anchor which employs an anchor body made of a flat fibrous material to facilitate insertion into the bone and transformation in shape.

In general, when damage (rupture) occurs in soft tissues such as tendons, ligaments, and muscles, or when soft tissues are broken, a surgical method of attaching and fixing the soft tissues of the damaged part to a bone is used.

For example, as the sports or leisure population increases, when a rotator cuff is diagnosed as a rupture and undergoes surgery, the damaged part is removed and a normal rotator cuff is fixed to the bone for treatment.

In this case, to fix soft tissues such as rotator cuffs to the bone, the soft tissues can be attached and fixed to the bone by making a hole in the bone, inserting an anchor into the hole, and tying a suture connected to the anchor to the soft tissues.

For example, a method of bolting a bolt-shaped anchor with a screw thread to a bone has been used conventionally as introduced in Korean Patent Publication No. 2015-0136707 and Korean Patent Publication No. 2015-0126855.

However, due to differences in bone density, etc., a screw thread formed in the bone and a screw thread formed in the anchor do not exactly match, and as time passes, the anchor becomes loose, and the suture also becomes loose. This causes a problem in that the soft tissues cannot be held firmly.

In addition, it is difficult to form a screw hole in the bone using a surgical drill, and a doctor may feel a sense of rejection while bolting the anchor with a surgical driver. Patients can also feel a sense of heterogeneity due to the insertion of the metal anchor.

Accordingly, Korean Patent No. 10-1634796 entitled 'Omega knot type sleeve anchor' has proposed, as shown in FIG. 1, a method of fastening a suture 40 into through-holes 23 and 30 formed at both ends of an anchor body 10, inserting the anchor body 10 into a bone, and pulling the suture 40 to implement anchoring by shape transformation.

That is, after the anchor body 10 to which the suture is fastened is bent in an approximately U shape as shown in FIG. 2 (a), it is inserted into the perforated bone as shown in FIG. 2 (b), and both ends of the suture 40 is pulled from the outside of the bone as shown in FIG. 2 (c).

Therefore, as shown in FIG. 2 (d), both ends of the anchor body 10 are caught inside the bone and thereby transformed into an omega (Ω) shape as a whole, which has a larger area than the perforated hole and thus anchoring is made.

However, in the above-described Korean Patent No. 10-1634796, if the shape is not transformed into a complete omega shape, it can be anchored for a long time in the bone, and if the suture is pulled with a certain amount of force or more, there is a risk of separation.

In addition, it is difficult to transform the anchor body 10 by pulling the suture because the anchor body 10 has a hollow tube structure, and rapid anchoring is difficult because a large force is required for work.

SUMMARY OF THE INVENTION

In order to solve the above-described problems, the present invention provides a flat-type sleeve anchor that is inserted into a bone and then transformed in shape to fix soft tissues such as muscles to the bone.

In particular, the present invention provides a flat-type sleeve anchor that adopts an anchor body made of a fibrous material which allows an easy insertion into the bone and also realizes an easier and more robust anchoring because transformation is made through being folded or bent to corrugate.

A flat-type sleeve anchor according to the present invention includes an anchor body having a predetermined length and width and made of a fibrous material; a suture fastened to the anchor body; an inlet hole formed at an inward position distanced from one end of the anchor body, allowing the suture to be inserted into the anchor body; an outlet hole formed at an inward position distanced from other end of the anchor body, allowing the suture inserted into the inlet hole to be drawn out; a plurality of tension holes formed to be spaced apart in a longitudinal direction of the anchor body between the inlet hole and the outlet hole, allowing the suture to sequentially pass through the anchor body in a backstitch manner, and allowing the anchor body to be transformed in shape when both ends of the suture are pulled; and a knot thread binding both ends of the anchor body together after the anchor body is folded in half to be inserted into the perforated bone.

In the flat-type sleeve anchor, the number of the tension holes may be six, length and width of the anchor body 110 may have a ratio of 30±4.5 mm to 5±1 mm, a length between two tension holes 133-3 and 133-4 disposed in a center of a longitudinal direction among the tension holes 133 may be 4±0.5 mm, each of a length from the one end of the anchor body 110 to the inlet hole 131 and a length from the other end to the outlet hole 132 may be 4±0.5 mm, and each of a length between the inlet hole 131 and a tension hole 133-1 adjacent to the inlet hole 131, a length between the outlet hole 132 and a tension hole 133-6 adjacent to the outlet hole 132, and a length between remaining tension holes excluding the two tension holes 133-3 and 133-4 disposed in the center may be 3±0.5 mm.

In addition, one side of the suture inserted into the inlet hole and other side of the suture drawn out from the outlet hole may be disposed above the knot thread that binds the anchor body.

In addition, the suture may be formed of one strand, two strands, or three strands, and the strand(s) of the suture may be fastened together to the inlet hole, the outlet hole, and the tension holes.

In addition, when the suture is formed of two or three strands, each of the inlet hole, the tension holes, and the outlet hole may be formed in two or three spaced apart in a width direction of the anchor body.

Advantageous Effects

According to the present invention, the flat-type sleeve anchor is inserted into the bone and then transformed in shape to fix soft tissues such as muscles to the bone. In particular, adopting the anchor body made of a fibrous material allows an easy insertion into the bone and also realizes an easier and more robust anchoring because transformation is made through being folded or bent to corrugate.

DETAILED DESCRIPTION OF THE INVENTION

Hereinafter, a flat-type sleeve anchor according to embodiments of the present invention will be described in detail with reference to the accompanying drawings.

Figure 3:
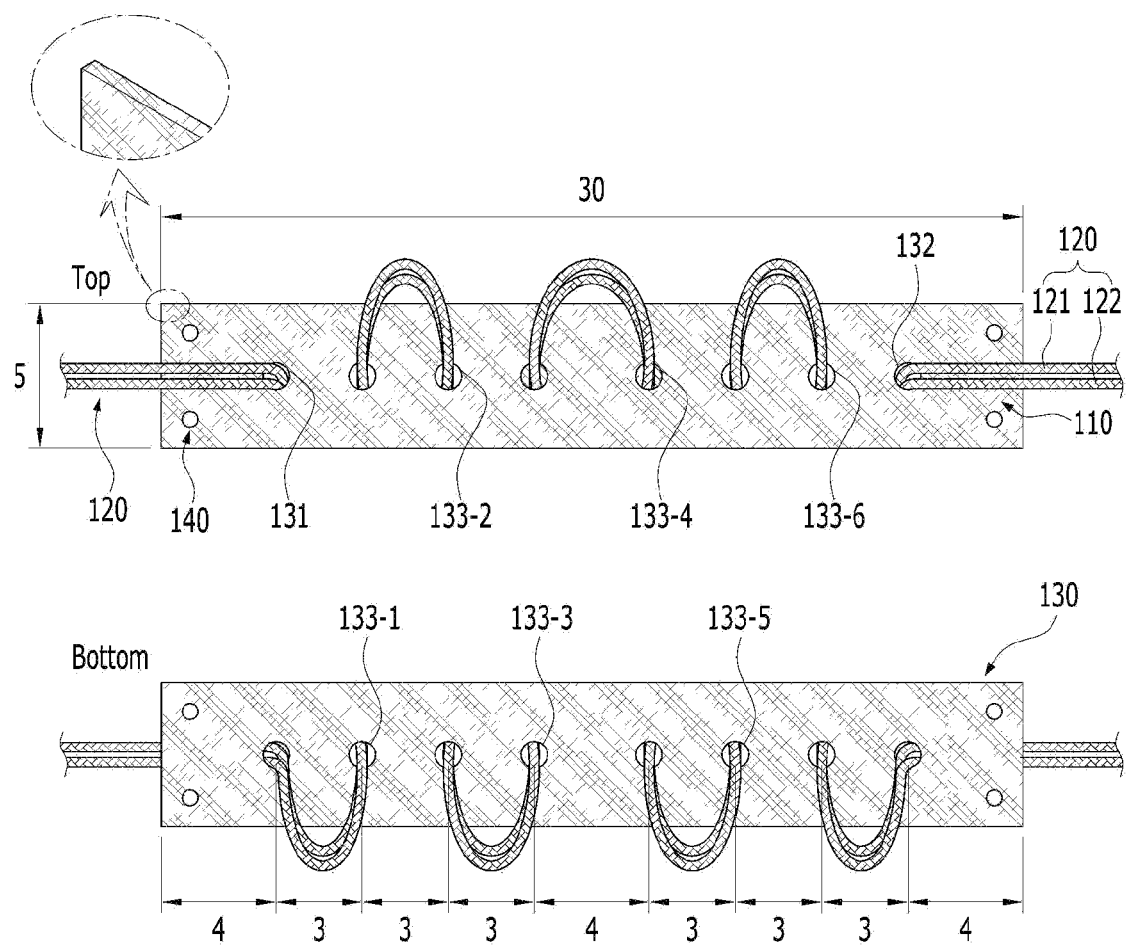
FIG. 3 is a plan view showing a flat-type sleeve anchor (two strands of suture) according to a first embodiment of the present invention.
Figure 4:
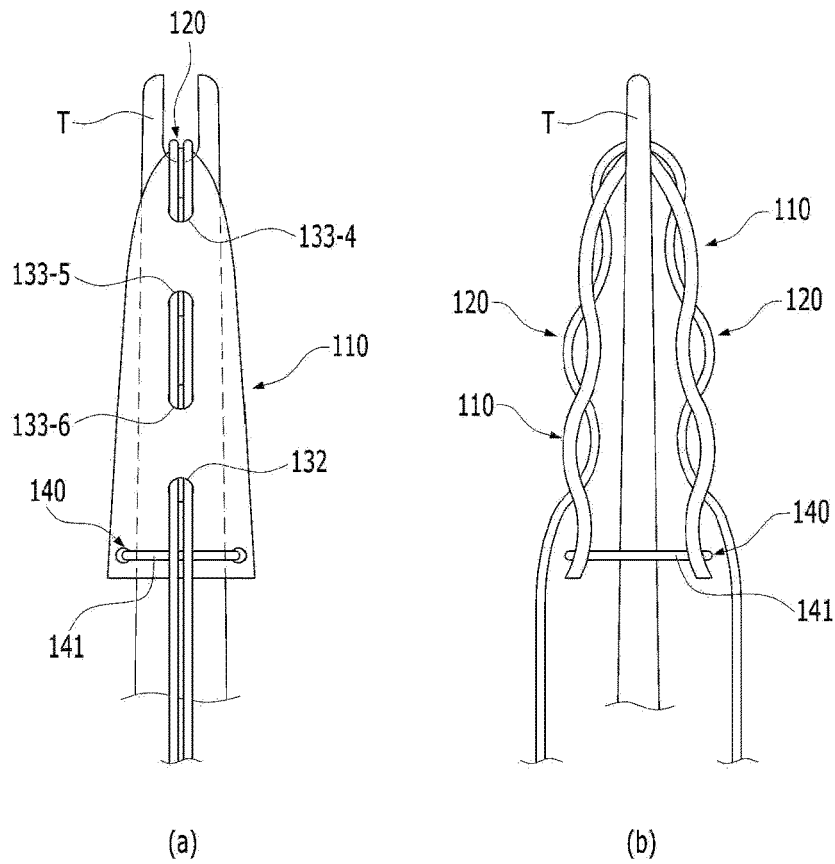
FIG. 4 is a view showing the state of insertion into the bone of FIG. 3.

As shown in FIGS. 3 and 4, the flat-type sleeve anchor according to the first embodiment of the present invention is a sleeve anchor to be fixed inside a bone, and includes an anchor body 110, a suture 120, an inlet hole 131, an outlet hole 132, tension holes 133, and a knot thread 141.

The anchor body 110 is made of a fibrous material and is thus transformed in shape after being inserted into a perforated bone during surgery for fixing soft tissues (e.g., tendons, ligaments, muscles, etc.) to the bone. This shape transformation occurs when the suture 120 fastened to the anchor body 110 is pulled.

The inlet hole 131, the outlet hole 132, and the tension holes 133 allow the suture 120 to be fastened to the anchor body 110. Among them, the inlet hole 131 is formed near one end of the anchor body 110, the outlet hole 132 is formed near the other end of the anchor body 110, and the plurality of tension holes 133 are formed between the inlet hole 131 and the outlet hole 132.

The knot thread 141 binds both ends of the anchor body 110 folded in half so as not to be released (see FIG. 4), thereby preventing loosening and also enabling stable transformation when the anchor body 110 is transformed.

According to this configuration, when the anchor body 110 is folded in half so as to be approximately U-shaped and then inserted into the bone, and when the suture 120 is pulled, the anchor body 110 is transformed and thereby its volume (or cross-sectional area) becomes larger than an insertion hole formed in the bone.

Therefore, the anchor body 110 is fixed (i.e., anchored) inside the bone, and the suture 120 fixed to the bone through the anchor body 110 binds and fixes damaged soft tissues such as tendons, ligaments, and muscles to treat the soft tissues.

In particular, the present invention adopts the anchor body 110 made of a fibrous material, which allows an easy insertion into the bone and also realizes an easier and more robust anchoring because transformation is made through being folded or bent to corrugate.

To this end, the anchor body 110 has a flat-type shape different from a conventional hollow tube-type body and has a predetermined length and width. In particular, the anchor body 110 is provided in a fabric state of woven fibers.

Therefore, the anchor body 110 can be folded into an approximately U shape and then inserted into the bone. After insertion, the anchor body 110 is transformed in shape by a larger volume than the entrance of the insertion hole perforated in the bone when the suture 120 is pulled.

For example, when the anchor body 110 made of fiber (fabric) is inserted into the bone and then the suture 120 is pulled, the anchor body 110 is folded into a wave or corrugated shape and resultantly bundled. Thus, the cross-sectional volume increases and a kind of a bundle shape is obtained.

The anchor body 110 may use fiber yarn materials such as polyethylene (PE), e.g., ultra-high molecular weight PE (UHMWPE), polyethylene terephthalate (PET), nylon, and polypropylene (PP).

The suture 120 sequentially passes through the inlet hole 131, the tension holes 133, and the outlet hole 132, which are formed in the anchor body 110, and is fastened to the anchor body 110. Both ends of the suture 120 maintains a state of being drawn from left and right portions of the anchor body 110.

For this, while the length of the anchor body 110 is for example 30 mm, the length of the suture 120 is about 950 mm, and both ends of the suture 120 are located outside the perforated bone during surgery. Therefore, after inserting the anchor body 110, the surgeon can pull the suture 120 outside the bone.

As the suture 120, a mixed material of UHMWPE and polyester may be used, for example. In addition, the suture 120 may be formed of a monofilament or by twisting two or more filaments. In case of being formed by twisting two or more filaments, the suture 120 has good elasticity and is easy to handle and knot compared to the other case of using a monofilament.

In the first embodiment of the present invention, two strands of a suture 120, each of which is formed of one monofilament or two or more twisted filaments, are used. Two strands 121 and 122 of the suture are fitted together to pass through the inlet hole 131, the tension holes 133, and the outlet hole 132.

The inlet hole 131, the outlet hole 132, and the tension holes 133 allow the suture 120 to be inserted into the anchor body 110. The inlet hole 131 is formed at an inward position slightly distanced from one end of the anchor body 110, allowing the suture 120 to start to be inserted into the anchor body 110.

On the contrary, the outlet hole 132 is formed at an inward position slightly distanced from the other end of the anchor body 110 (opposite to the inlet hole), allowing the suture 120 inserted into the inlet hole 131 to be finally drawn out. The tension holes 133 to be described below are provided between the inlet hole 131 and the outlet hole 132.

The plurality of tension holes 133 are formed to be spaced apart in a longitudinal direction of the anchor body 110 between the inlet hole 131 and the outlet hole 132. The suture 120 inserted through the inlet hole 131 sequentially passes through the tension holes 133 and then is drawn out through the outlet hole 132.

The suture 120 is sequentially fitted into the tension holes 133 of the anchor body 110 in a backstitch manner, for example. That is, the suture 120 passes through the plurality of tension holes 133 from the top of the anchor body 110 to the bottom of the anchor body 110 and then from the bottom to the top.

Therefore, when one end of the suture 120 extended outwardly from the inlet hole 131 and the other end of the suture 120 extended outwardly from the outlet hole 132 are simultaneously pulled, the suture 120 inserted in the tension holes 133 applies tension to the flat-type anchor body 110 made of a fibrous material, thereby causing shape transformation.

The shape transformation may vary slightly depending on a force or direction of pulling the suture 120. However, because the anchor body 110 is folded into a wave or corrugated shape as described above, the shape transformation is made resultantly into a bundle form.

It is preferable that the number of tension holes 133 (133-1 to 133-6) is six from the first tension hole 133-1 to the sixth tension hole 133-6. In this case, the length and width of the anchor body 110 have a ratio of 30±4.5 mm to 5±1 mm in a preferred embodiment.

In addition, the length between two tension holes 133-3 and 133-4 disposed in the center of the longitudinal direction among the tension holes 133 is 4±0.5 mm. Also, each of the length from one end of the anchor body 110 to the inlet hole 131 and the length from the other end to the outlet hole 132 is set to 4±0.5 mm.

In addition, it is preferable that each of the length between the inlet hole 131 and the tension hole 133-1 adjacent to the inlet hole 131, the length between the outlet hole 132 and the tension hole 133-6 adjacent to the outlet hole 132, and the length between the remaining tension holes excluding the two tension holes 133-3 and 133-4 disposed in the center is 3±0.5 mm.

Therefore, holes are formed at intervals of 4±0.5 mm, 30±4.5 mm, 30±4.5 mm, 30±4.5 mm, 4±0.5 mm, 30±4.5 mm, 30±4.5 mm, 30±4.5 mm, and 4±0.5 mm from one end of the anchor body 110 near the inlet hole 131 to the other end near the outlet hole 132.

Therefore, when the anchor body 110 is folded and inserted, the suture 120 having a length of 4±0.5 mm disposed in a central portion of the anchor body in the longitudinal direction is caught and supported by a front end hook of a surgical tool (see 'T' in FIG. 4), and both side portions of the anchor body are stitched at intervals of 30±4.5 mm with the suture 120. This allows the shape transformation to be stably made.

In addition, because the inlet hole 131 and the outlet hole 132 are formed 4±0.5 mm apart from both ends of the anchor body 110 inward, respectively, the anchor body 110 can be folded into a wave or corrugated shape and also transformed into an omega-like shape.

Figure 1:
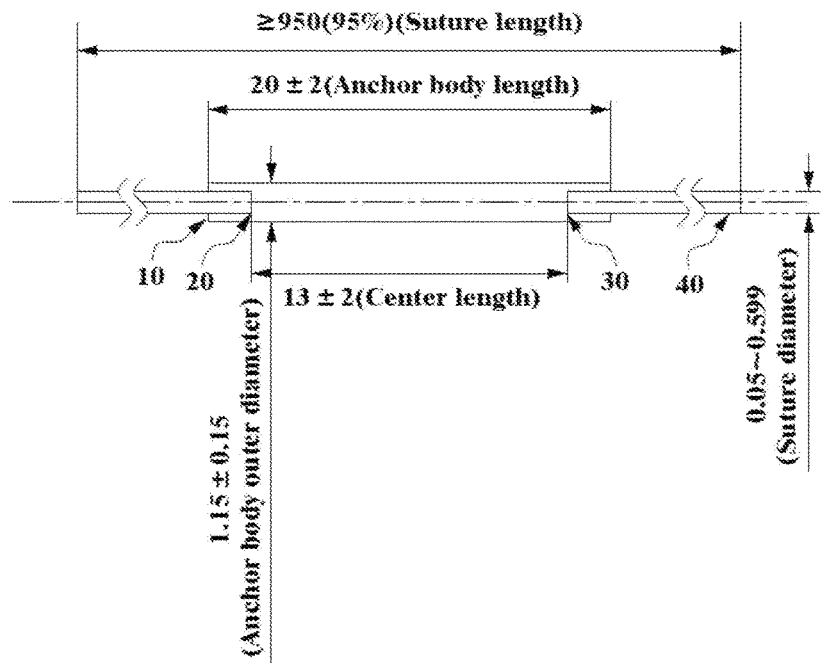
FIG. 1 is a view showing an omega knot-type sleeve anchor according to the prior art.
Figure 2:
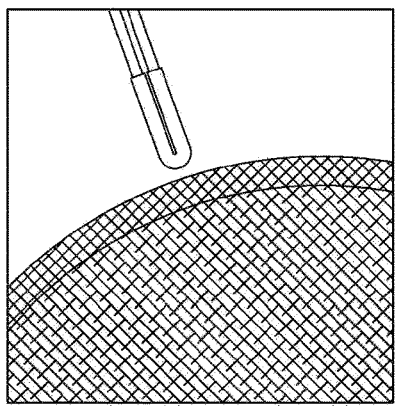
FIGS. 2A to 2D are views illustrating shape-deformed states of FIG. 1.
Figure 2:
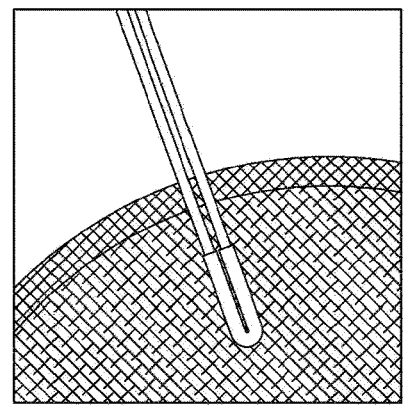
Figure 2:
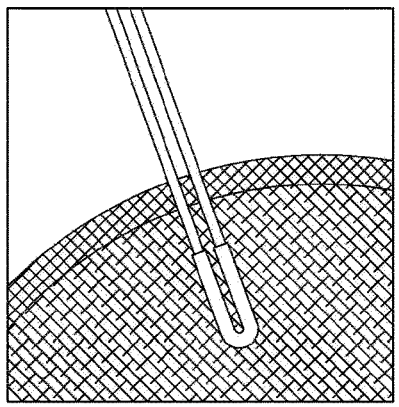
Figure 2:
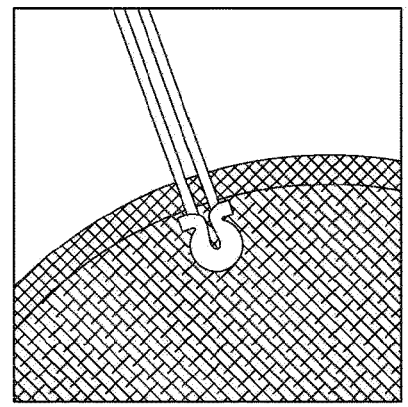

That is, an upper part of the anchor body is transformed into a circular shape and a lower part is bent outward, based on the inlet hole 131 and the outlet hole 132. Therefore, it is transformed into an omega (Ω) shape as described in FIG. 2D.

In particular, the present invention is differentiated from the prior art in that a flat-type fibrous material is used for the anchor body 110 and thus, due to the characteristics of the material and shape, a wave or corrugation is additionally formed in an upper circular portion of the omega shape.

Meanwhile, (a) of FIG. 4 is a front view showing a state in which using a surgical tool (T) the anchor body 110 is folded in half and inserted into the bone, and (b) of FIG. 4 is a side view looking at the side of (a) of FIG. 4.

As shown, after the anchor body 110 is folded in half to be inserted into the perforated bone, the knot thread 141 binds both ends of the anchor body 110 together.

Therefore, the knot thread 141 fixedly holds the ends of the anchor body 110 folded in half, and enables a stable shape transformation of the anchor body 110 when the suture 120 is pulled for transformation.

On the other hand, as also shown in FIG. 3, both ends of the anchor body 110 may have auxiliary holes 140 into which the knot thread 141 is inserted. The auxiliary holes 140 may be formed by artificially drilling holes in the anchor body 110 with a separate tool, or formed naturally when stitching with the knot thread 141.

In addition, as shown in FIG. 4, both side portions of the suture 120 are preferably disposed to overlap over the knot thread 141. Specifically, it is desirable that one side of the suture 120 inserted into the inlet hole 131 and the other side of the suture 120 drawn out from the outlet hole 132 are disposed above the knot thread 141 that binds the anchor body 110.

Therefore, even if the doctor pulls the suture 120, the suture 120 disposed outside the knot thread 141 does not pull the knot 141. This prevents the knot thread 141 from being loosened or pulled, thereby enabling a stable shape transformation without limiting the movement of the suture 120.

Hereinafter, a flat-type sleeve anchor according to other embodiments of the present invention will be described in detail with reference to the accompanying drawings.

Figure 5:
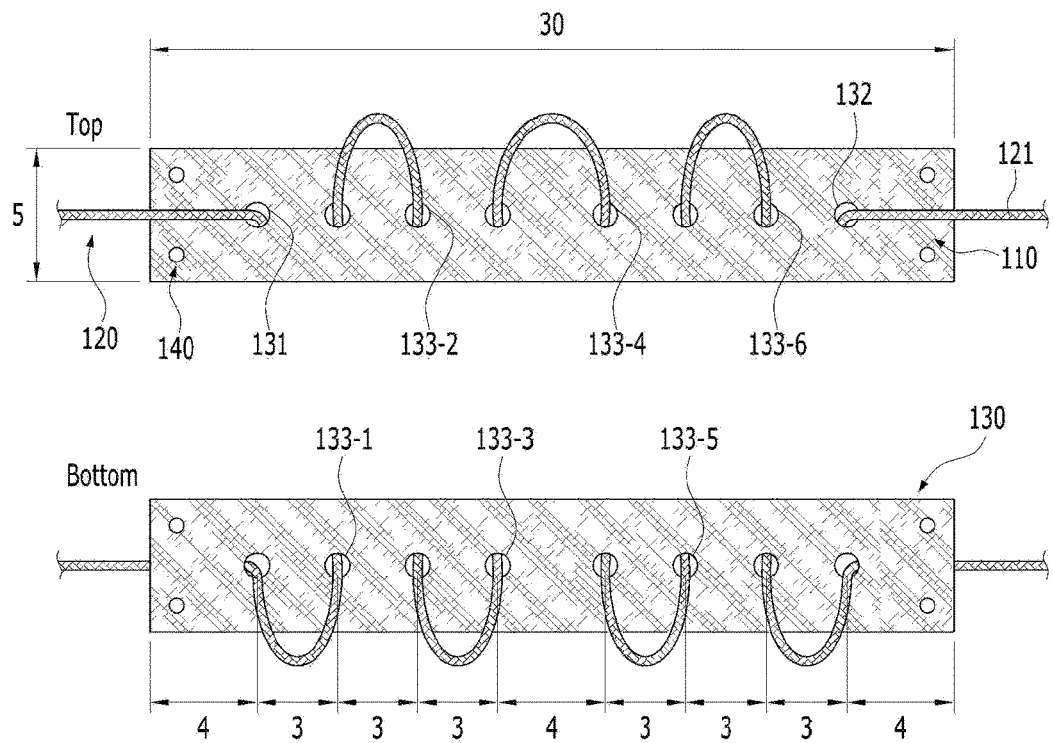
FIG. 5 is a plan view showing a flat-type sleeve anchor (one strand of suture) according to a second embodiment of the present invention.
Figure 6:
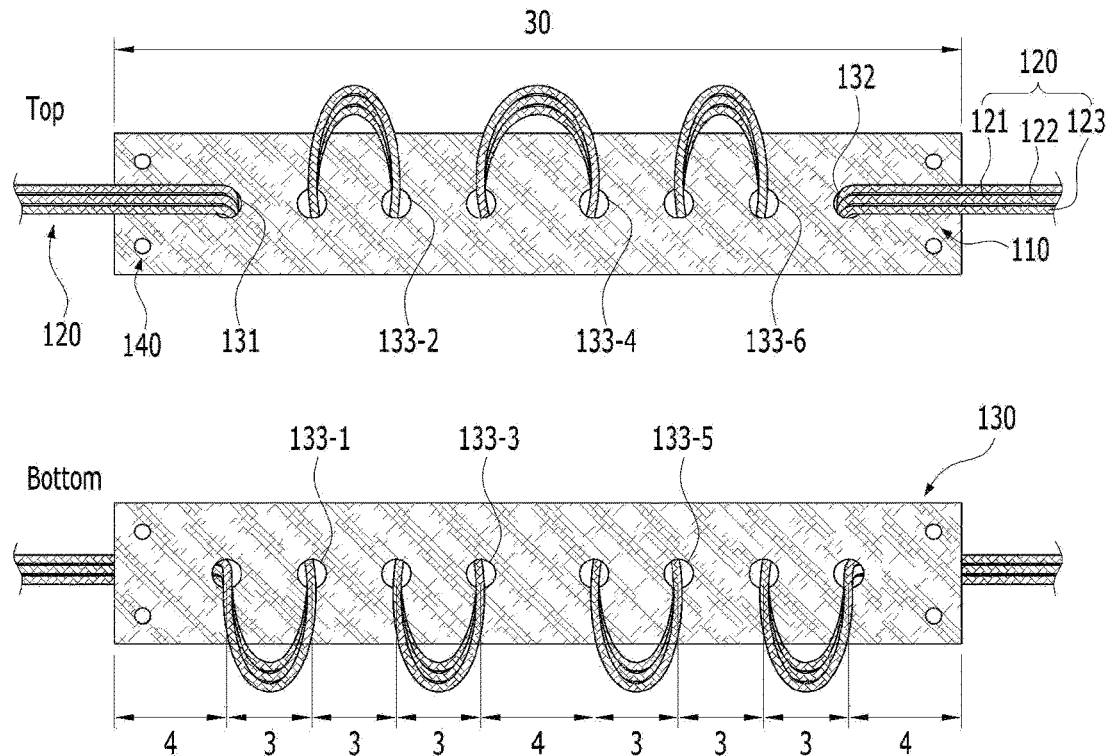
FIG. 6 is a plan view showing a flat-type sleeve anchor (three strands of suture) according to a third embodiment of the present invention.

As shown in FIGS. 5 and 6, the flat-type sleeve anchor according to other embodiments of the present invention includes the anchor body 110, the suture 120, the inlet hole 131, the outlet hole 132, the tension holes 133, and the knot thread 141. This configuration is as described above.

However, the suture 120 may be formed of only one strand 121 as in the second embodiment of the present invention shown in FIG. 5, or the suture 120 may be formed of three strands 121, 122, and 123 as in the third embodiment of the present invention shown in FIG. 6.

In addition, in the present invention described with reference to FIGS. 3 to 6, when the suture 120 is formed of two or three strands as well as when the suture 120 is formed of a single strand, such strands of the suture 120 are fastened together to the inlet hole 131, the outlet hole 132, and each tension hole 133.

Figure 7:
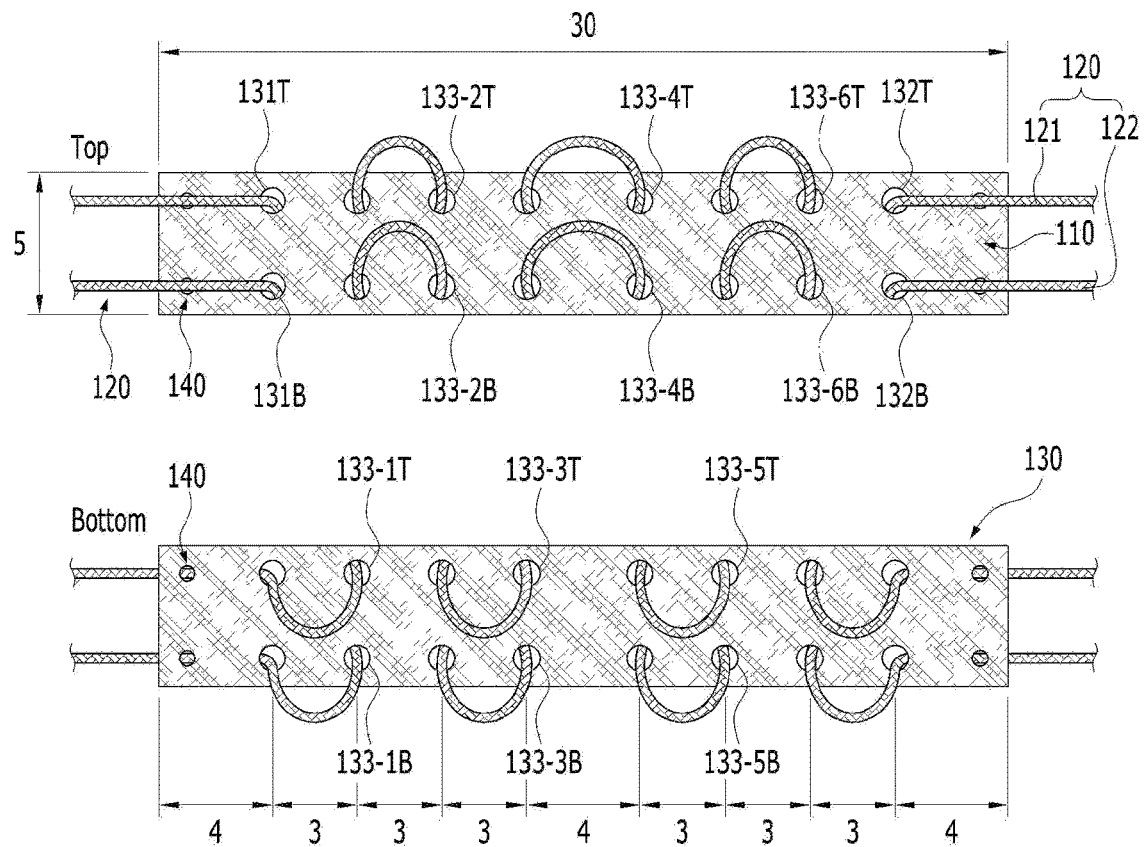
FIG. 7 is a plan view showing a flat-type sleeve anchor (individually inserted suture) according to a fourth embodiment of the present invention.

However, in the fourth embodiment of the present invention as shown in FIG. 7, when the suture 120 is formed of two or three strands, each of the inlet hole 131, the tension hole 133, and the outlet hole 132 is formed in two or three spaced apart in a width direction of the anchor body 110, resultantly forming a plurality of rows.

For example, when the suture 120 is formed of two strands, two inlet holes 131T and 131B and two outlet holes 132T and 132B are formed, and also each tension hole formed at each position is separated into two tension holes such as 133-1T and 133-1B. Thus, one strand of suture 120 is separately fastened in each row.

Therefore, when the anchor body 110 is transformed in shape by using the sutures 121 and 122 fitted in the inlet holes 131T and 131B, the tension holes such as 133-1T and 133-1B, and the outlet holes 132T and 132B sequentially disposed in the longitudinal direction, a more stable and sufficient amount of transformation is provided due to the plurality of outlet holes 132T and 132B spaced apart in the width direction of the anchor body 110.

While the present invention has been particularly described and shown with reference to exemplary embodiments thereof and drawings, but this is only provided to help a better understanding of the present invention. The present invention is not limited to such embodiments, and various modifications and variations are possible from the descriptions as being apparent to those skilled in the art.

Accordingly, the scope of the present invention should not be limited to the described embodiments, and all the appended claims and their equivalents fall within the scope of the present invention.

The invention claimed is:

1. A flat-type sleeve anchor that is transformed in shape and fixed after being inserted into a perforated bone to fix soft tissues to the bone, the flat-type sleeve anchor comprising:
   an anchor body (110) having a predetermined length and width and made of a fibrous material;
   a suture (120) fastened to the anchor body (110);
   an inlet hole (131) formed at an inward position distanced from one end of the anchor body (110), allowing the suture (120) to be inserted into the anchor body (110);
   an outlet hole (132) formed at an inward position distanced from other end of the anchor body (110), allowing the suture (120) inserted into the inlet hole (131) to be drawn out;
   a plurality of tension holes (133) formed to be spaced apart in a longitudinal direction of the anchor body (110) between the inlet hole (131) and the outlet hole (132), allowing the suture (120) to sequentially pass through the anchor body (110) in a backstitch manner, and allowing the anchor body (110) to be transformed in shape when both ends of the suture (120) are pulled; and
   a knot thread (141) binding both ends of the anchor body (110) together after the anchor body (110) is folded in half to be inserted into the perforated bone.

2. The flat-type sleeve anchor of claim 1, wherein the number of the tension holes (133) is six,
   wherein length and width of the anchor body (110) have a ratio of 30±4.5 mm to 5±1 mm,
   wherein a length between two tension holes (133-3 and 133-4) disposed in a center of a longitudinal direction among the tension holes (133) is 4±0.5 mm,
   wherein each of a length from the one end of the anchor body (110) to the inlet hole (131) and a length from the other end to the outlet hole 132 is 4±0.5 mm, and
   wherein each of a length between the inlet hole 131 and a tension hole (133-1) adjacent to the inlet hole (131), a length between the outlet hole (132) and a tension hole (133-6) adjacent to the outlet hole (132), and a length between remaining tension holes excluding the two tension holes (133-3 and 133-4) disposed in the center is 3±0.5 mm.

3. The flat-type sleeve anchor of claim 1, wherein one side of the suture (120) inserted into the inlet hole (131) and other side of the suture (120) drawn out from the outlet hole (132) are disposed above the knot thread (141) that binds the anchor body (110).

4. The flat-type sleeve anchor of claim 1, wherein the suture (120) is formed of one strand, two strands, or three strands, and the strand(s) of the suture (120) are fastened together to the inlet hole (131), the outlet hole (132), and the tension holes (133).

5. The flat-type sleeve anchor of claim 4, wherein when the suture (120) is formed of two or three strands, each of the inlet hole (131), the tension holes (133), and the outlet hole (132) is formed in two or three spaced apart in a width direction of the anchor body (110).

* * * * *